United States Patent [19]

Derderian et al.

[11] Patent Number: 4,553,852
[45] Date of Patent: Nov. 19, 1985

[54] APPARATUS AND METHOD FOR HEAT FLOW MEASUREMENT

[75] Inventors: Gregory Derderian, Arlington; Robert D. Orlandi, Tewksbury; Larry S. Shu, Newton Highlands; Bahram Siadat, Boxboro, all of Mass.

[73] Assignee: W. R. Grace & Co., Lexington, Mass.

[21] Appl. No.: 558,750

[22] Filed: Dec. 7, 1983

[51] Int. Cl.$^4$ .................................... G01K 17/00
[52] U.S. Cl. ............................... 374/1; 374/30; 374/10; 374/43
[58] Field of Search ............... 374/1, 2, 10, 29, 30, 374/43, 44, 134

[56] References Cited

U.S. PATENT DOCUMENTS

| | | | |
|---|---|---|---|
| 3,045,473 | 3/1959 | Hager, Jr. | 374/44 |
| 3,194,071 | 7/1965 | Hager, Jr. | 374/134 |
| 4,198,859 | 4/1980 | Holtermann | 374/30 |

FOREIGN PATENT DOCUMENTS

| | | | |
|---|---|---|---|
| 0163395 | 6/1964 | U.S.S.R. | 374/1 |
| 0594416 | 2/1978 | U.S.S.R. | 374/1 |
| 0917092 | 3/1982 | U.S.S.R. | 374/1 |

OTHER PUBLICATIONS

Publication of H. F. Poppendiek "Why Not Measure Heat Flux Directly?", Environmental Quarterly, vol. 15, No. 1, Mar. 1969.
The Design and Construction of a Calibrated/Guarded Hot Box Facility, presented by E. L. Perrine et al. at the ASHRAE/DOE-ORNL Conference, Dec. 3, 1979.
Publication of S. N. Flanders et al., "In Situ Measurements of Masonry Wall Thermal Resistance", presented at the ASHRAE Annual Convention, Houston, Texas, on Jan. 24, 1982.
Publication of W. C. Brown et al., "In Situ Measurements of Frame Wall Thermal Resistance", presented at ASHRAE Annual Convention, Houston, Texas on Jan. 24, 1982.
The publication of Orlandi et al., "A Field Thermal Measurement Technique for Building Envelopes", presented at the ASHRAE/DOE Conference on Thermal Performance of the Exterior Envelope of Buildings II, Las Vegas, Nevada, on Dec. 8, 1982.

Primary Examiner—Charles Frankfort
Assistant Examiner—Thomas B. Will
Attorney, Agent, or Firm—John J. Wasatonic; William L. Baker

[57] ABSTRACT

A method for accurate, on site heat flow measurement through a substrate surface using surface mounted heat flow sensors and an apparatus for on site calibration of surface mounted heat flow sensors are presented. The method comprises mounting on the substrate surface a heat flow sensor which is calibrated to establish the relationship between heat flow through the surface and the resultant induced voltage in the sensor under the convective and radiative heat transfer environmental conditions of the surface, measuring the voltage output induced in the sensor by heat flow through the surface, and converting the voltage output to a quantitative heat flow on the basis of the calibration of the sensor. The apparatus of the invention permits the calibration of the sensors under convective and radiative heat transfer environmental conditions which substantially duplicate those of the experimental substrate.

19 Claims, 4 Drawing Figures

APPARATUS AND METHOD FOR HEAT FLOW MEASUREMENT

BACKGROUND OF THE INVENTION

This invention relates to a method and an apparatus for determining heat flow through a substrate. More particularly, this invention relates to an apparatus for field calibration of heat flow sensors and to a method for accurately measuring heat flow in the field utilizing field calibrated heat flow sensors.

Reliable quantitative thermal performance (heat flow) measurements of existing building and roofdeck systems while exposed to conditions of actual use have heretofore proven difficult to obtain. Information from such measurements, if available, could be used to compare actual in-place performance with theoretically expected performance, e.g., of insulation systems and materials. In-place measurement would also provide information on peak energy loads and average energy losses for the particular system under the actual conditions of use. Improvements in the design and construction of building and roofdeck systems could materialize from such information.

Heat flow measurements have been previously made on various substrates such as walls and roofdecks utilizing commercially available heat flow sensors. These sensors are generally in the form of thin disks and comprise a very dense thermopile system capable of outputting a voltage signal related to an average temperature differential across the thickness of the disk. This voltage signal is converted to a quantitative heat flux, e.g., $BTU/h.ft^2$, on the basis of a calibration parameter for the sensors.

Generally, heat flow measurements with such sensors have been made with the sensor embedded in the substrate such that heat transfer is primarily, if not exclusively, by the conductive mode. Calibration of the sensor has heretofore been carried out under controlled, laboratory conditions. The calibration is typically conducted in a guarded hot plate or heat flow meter apparatus. The sensor is mounted on or embedded in a substrate mounted in the apparatus and calibrated by measurement of the voltage generated by the sensor in response to a known input of heat from a heat source within the apparatus. Calibration is normally conducted in accordance with ASTM-C177 in the guarded hot plate or C518 in the heat flow meter apparatus and may provide a satisfactory calibration parameter for use of the sensor when embedded in an experimental substrate since heat transfer under the calibration conditions is by conduction.

For purposes of providing reliable on site heat flow measurements, however, the practice of embedding the heat flow sensor in an experimental substrate, e.g., a wall of a room or a roofdeck, may not be satisfactory or practical. At least localized destruction of the substrate is required and the measurements obtained are unlikely to be representative of the actual substrate.

SUMMARY OF THE INVENTION

In its method aspects, the present invention is directed to a non-destructive heat flow measurement method utilizing surface mounted heat flow sensors. In using heat flow sensors mounted on the surface of the substrate, rather than embedded therein, the present method offers the advantages of avoiding destruction of the substrate and providing heat flow measurements at the specific boundary of interest under the actual environmental conditions to which that boundary (substrate surface) is subject.

The present method comprises mounting a heat flow sensor or, preferably, a cluster of heat flow sensors on the surface of a substrate which replicates the experimental substrate through which heat flow measurements are to be made, calibrating the mounted sensor under the heat transfer environmental conditions to which the experimental substrate is subject, removing the sensor and re-mounting it on the experimental substrate utilizing the same means of attachment as used for calibration purposes, conducting experimental measurements, and converting the experimental data to a quantitative heat flow on the basis of the aforementioned calibration.

From the above, the present method will be seen to include operative steps which provide on site calibration of the heat flow sensor. This practice derives from the discovery that the methods of calibrating heat flow sensors which have been heretofore used are not satisfactory where experimental measurements are to be made with the sensor mounted on the surface of the experimental substrate. More specifically, it has been found that under such usage conditions, the radiative and convective modes of heat transfer may predominate over the conductive mode to the extent that calibration under conditions of conductive heat transfer alone, i.e. conventional calibration methods, fails to provide a meaningful or useful calibration parameter. Rather, it has been determined that the heat flow sensor must be surface mounted and calibrated under heat transfer environmental conditions which replicate those under which experimental measurements are to be taken and which, therefore, include convective and radiative, as well as conductive, heat transfer modes.

In its product aspects, the present invention is directed toward a calibration apparatus which permits such on site calibration of surface mounted heat flow sensors. This apparatus can be designed and manufactured as a lightweight, portable unit which can be easily transported to the field measurement site and positioned in close proximity to the experimental measurement area for purposes of calibration under the aforementioned heat transfer conditions. The apparatus provides reliable calibration of heat flow sensors by providing a measured, uniform flow of heat through a specified area of a "test simulation" substrate, on which the heat flow sensors are mounted and which replicates the experimental substrate in geometry and heat transfer characteristics. Any of a variety of test simulation substrates can be provided as an element of the apparatus, so as to permit calibration for a corresponding variety of experimental substrates.

The apparatus and method of this invention are particularly useful for the measurement of heat flow across the interior surfaces of various roofdeck substrates, e.g. structural concrete or corrugated metal roofdecks.

The present invention is more fully described in the following detailed description, taken in connection with the accompanying drawings.

DETAILED DESCRIPTION OF THE INVENTION

Figure 1:
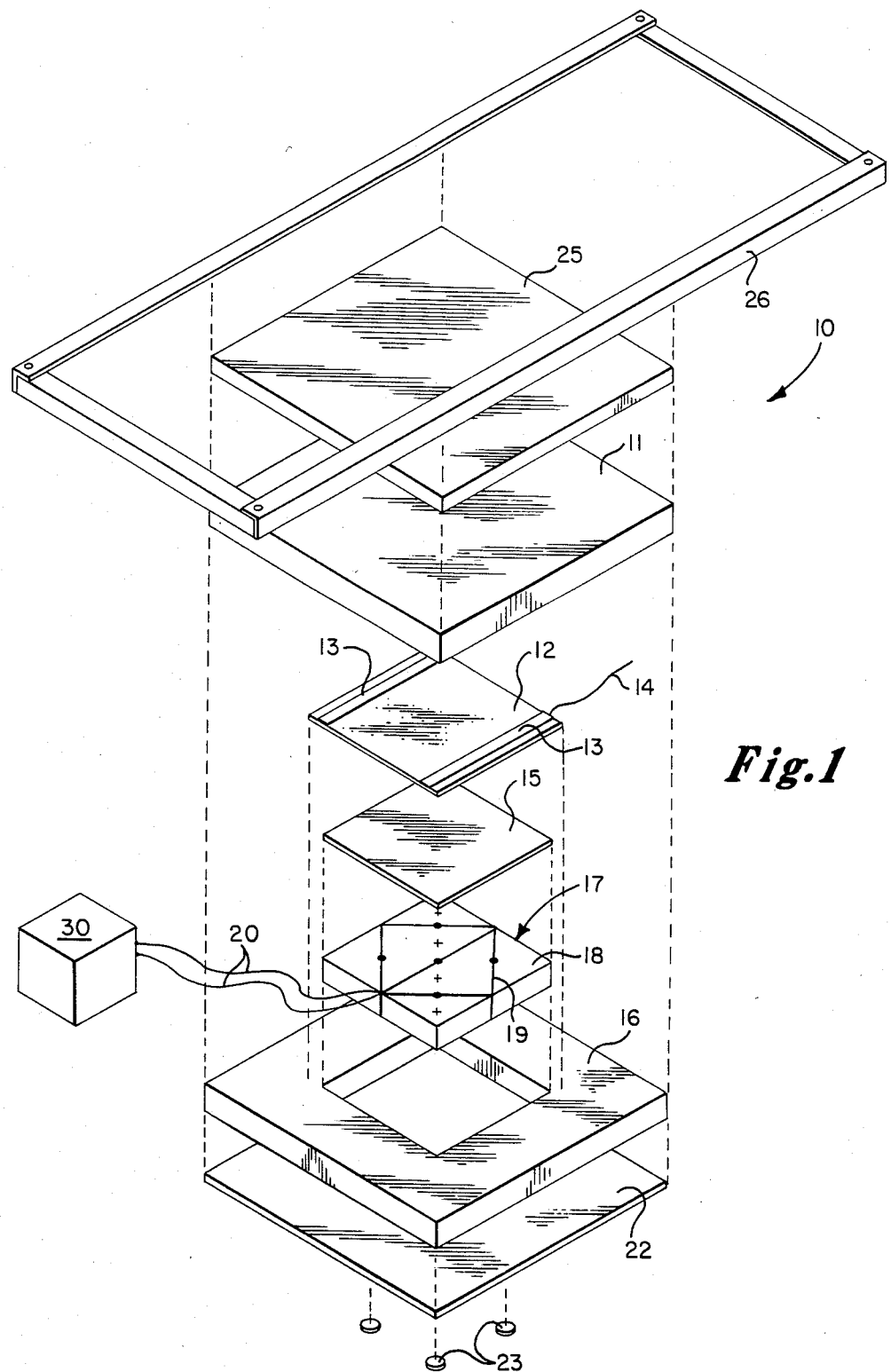
FIG. 1 is an exploded, perspective view of a preferred calibration apparatus of this invention.

Heat flowing through a substrate can be quantified by a heat flow sensor if the voltage output of the sensor in response to the heat flow is measured and the relationship between this voltage output and the heat flow is established. The determination of this relationship between the sensor voltage output and heat flow comprises the calibration of the heat flow sensor and the resultant mathematical relationship is commonly referred to as the calibration parameter.

The apparatus of this invention permits the determination of a calibration parameter for heat flow sensors which are surface mounted and, thus, exposed to convective and radiative heat transfer factors. The apparatus can be constructed as a lightweight, portable unit with a flat, relatively thin profile, such that it can be mounted in close proximity to the substrate on which experimental measurements are to be made, e.g., suspended from a roofdeck or mounted against a wall. The heat flow sensor which is to be calibrated is mounted on the exposed surface of the apparatus, i.e. that surface opposite the experimental substrate. This exposed surface replicates the experimental substrate in its geometry, e.g., flat or corrugated, and possesses to the extent possible the heat conductive and radiative properties of the experimental substrate surface i.e., it should be the same emittance and comprised of materials having similar heat conductivity. Since it simulates the experimental surface, this surface is referred to herein as a "test simulation surface". It is the external surface of a distinct layer of the apparatus, which is constructed from a uniform and thermally and mechanically stable material and is referred to herein as the "test simulation substrate" or "test simulation layer".

In mounting the heat flow sensor on the test simulation surface and in positioning this surface in close proximity to the experimental substrate, the heat flow sensor is placed in a heat transfer environment which substantially duplicates that which it is exposed to during experimental measurement, thereby permitting development of a meaningful and useful calibration parameter.

As further detailed below, the apparatus of this invention provides a means of generating different levels of a measured flow of heat through the test simulation layer. For purposes of calibration over a useful range, the heat flow through the test simulation layer is varied close to the approximate levels anticipated for the experimental substrate. The voltage output of the heat flow sensor, which is mounted on the test simulation surface, in response to the different levels of measured heat flow is measured, together with air and surface temperatures in the environment of the sensor. A calibration parameter is then calculated. This calibration parameter is defined as $\dot{q}/emf$, where $\dot{q}$ is the heat flux through the substrate and emf is the resultant voltage output of the sensor under a given set of environmental air and surface temperatures.

The apparatus of the invention comprises a layered arrangement of elements which are assembled as an integral unit with the respective elements in face-to-face contact. The apparatus comprises a heating element which is encased in an insulation envelope comprised of upper and lower insulation layers which have greater widthwise and lengthwise dimensions than the heating element and which are positioned in face to face relation, with the heating element therebetween. The test simulation substrate is affixed to the outer face of one of the insulation layers. This same insulation layer comprises a heat flow meter which occupies an interior area of the insulation layer, hereinafter referred to as the "heat flow metering area", and measures heat flow across this area. Preferably, the heat flow meter comprises a separate panel-like substrate wrapped with a thermopile which measures a voltage signal induced by the temperature differential between the opposed major surfaces of the panel. This temperature differential is converted to a quantitative heat flow based on prior calibration of the heat flow meter using known methods, e.g., ASTM-C518. The panel is comprised of the same material and has the same thickness as the insulation layer and is closely fitted into an aperture in the insulation layer. The test simulation layer is affixed to this insulation layer such that the measured heat flow across the heat flow meter is also that which passes through the test simulation layer to the heat flow sensors mounted thereon. (As used herein, the term "heat flow sensor" refers to the measurement device which is to be calibrated according to the invention. The term "heat flow meter" refers to that component of the apparatus which is calibrated by conventional means and is used to measure the heat flow generated by the apparatus for purposes of calibrating the heat flow sensors.)

The apparatus of this invention further comprises a heat conductive layer which is positioned between the heater element and the heat flow meter. This layer functions to distribute heat generated by the heater element uniformly across the area of the heat flow metering area, thereby providing a relatively large area of uniform heat flow and facilitating accurate calibration of a cluster of heat flow sensors mounted in alignment with this area.

In terms of relative dimensions, the heating element preferably is slightly greater in size (length and width) than the heat conductive layer. The heat conductive layer should have a length and width at least as great as that of the heat flow metering area. The heating element, conductive layer, heat flow metering area and that area of the test simulation surface on which the heat flow sensors are mounted are superposed so as to provide a linear pathway for heat flow from the heating element to the heat flow sensors.

Figure 3:
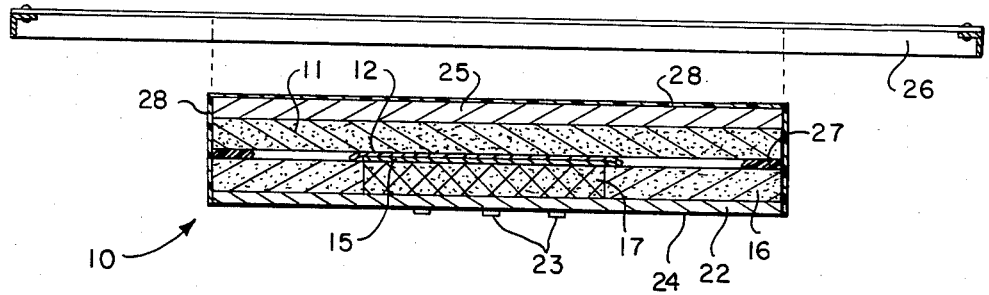
FIG. 3 is a sectional side elevational view of the apparatus of FIG. 1 after assembly.

Referring to the FIGURES, there is shown in FIG. 1 an exploded perspective view of a preferred calibration apparatus of this invention. FIG. 1 illustrates a calibration apparatus 10 consisting of a first insulation layer 11, a heating element 12 which is a flat flexible sheet-like element having conductive strips 13 bonded thereto adjacent to opposed edges of the element with leads 14 (one shown) extending from the strips 13, a heat conductive layer 15, and a second insulating layer 16. As shown in FIG. 1, the layers 11 and 16 have identical dimensions, although this is not a limitation of the present invention. The layers should, however, each have a lengh and width greater than that of the heating element (as shown in FIG. 1) such that the heating element and heat conductive layer are encased within the insulation layers when the layers are brought into face-to-face relation. This encasement is best shown in the sectional elevational view of apparatus 10 in FIG. 3, wherein like numerals refer to like elements. In FIG. 3, heating element 12 and conductive layer 15 are shown encased between layers 11 and 16, these facing surfaces of these layers being bonded together about their periphery by a suitable bonding agent, shown as 27, such as an epoxy adhesive. The complete encasement of heating element 12 and plate 15 is highly advantageous in that lateral heat flow is minimized, facilitating a steady state heat flow normal to the plane of the heat flow meter.

Figure 2:
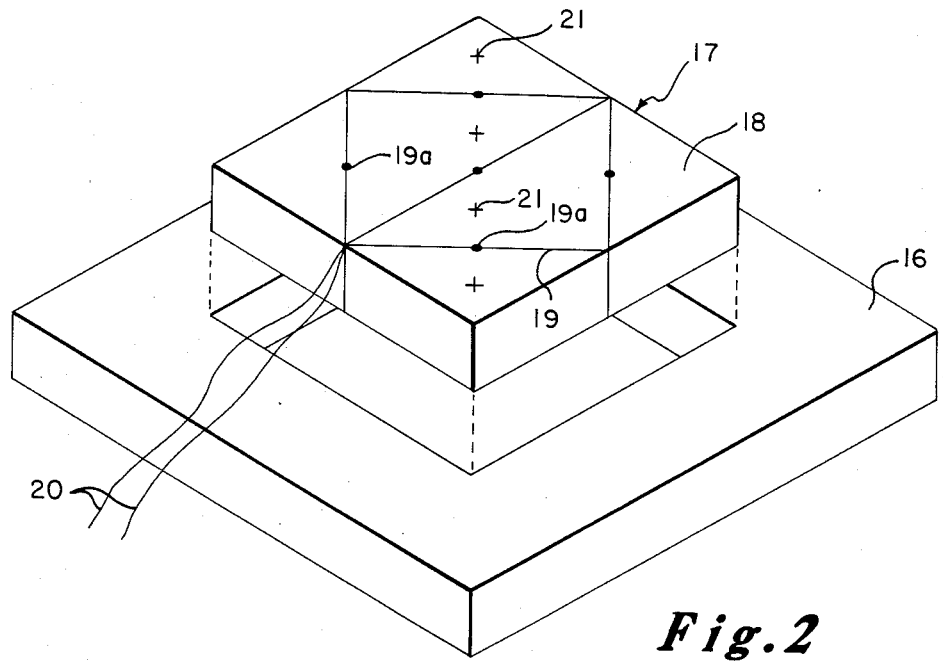
FIG. 2 is an exploded, perspective view of the heat flow meter element and associated insulation layer of the apparatus of FIG. 1.

As shown in FIG. 1, insulation layer 16 includes a centrally located heat flow meter 17 which is the same thickness as layer 16 and closely fits into the centrally located aperture in that layer. The structure of the heat flow meter and its association with the remainder of layer 16 are more clearly illustrated in FIG. 2, wherein like numerals refer to like elements. FIG. 2 shows the meter 17 to include a panel-like substrate 18 having a thermopile 19 wrapped thereabout. Thermopile 19 measures a voltage signal induced by the average temperature differential between the major surfaces of panel 18 and comprises a plurality of series connected thermocouples. The thermopile 19 is so constructed and wrapped about the panel 18 as to provide identical symetrical arrangements of the thermocouple junctions on both major surfaces of panel 18. The illustrated thermopile comprises ten junctions, each junction being formed by butt welding of the two dissimilar metals of the thermocouple system. Five junctions, indicated as points 19a, are symetrically arranged on the upper surface of panel 18 and the remaining five (not shown) are identically positioned on the lower surface of the panel.

Panel 18 is adapted to be closely inserted into the aperture provided in layer 16. In general, the panel is originally cut out from the layer 16 and then used in manufacturing the heat flow meter.

Thermopile 19 is also so constructed and wrapped about panel 18 such that the leads 20 extend from the same point on the heat flow meter and comprise the same metal. Most preferably, a copperconstantan series connected thermopile is employed with both leads being copper. After insertion of meter 17 into layer 16, the leads 20 are run along the upper surface of layer 16 as shown in FIG. 1 and extend through the bond 27 to a datalogger 30 which monitors the voltage output of the meter in response to the aforementioned temperature differential.

The voltage output of the heat flow meter is converted to a heat flow quantity on the basis of prior calibration of the heat flow meter by known methods, e.g., ASTM-C518. Calibration is preferably accomplished using a Rapid k Thermal Conductivity Instrument, manufactured by Dynatech Corporation, Cambridge, Mass., in accordance with ASTM-C518. For this calibration, a one foot by one foot heat flow meter is required.

Calibration of the heat flow meter requires that a steady, known heat flow be established across the thickness of the meter with a temperature differential resulting between the upper and lower surfaces of the meter. The voltage output of the thermopile which is generated by this temperature differential is measured to establish the relation between heat flow and voltage output of the meter and, thus, calibrate the meter. The resultant calibration parameter defines $\dot{q}/emf$ for the heat flow meter, where $\dot{q}$ is the known heat flux through the meter and emf is the voltage output of the thermopile. It is known however, that $\dot{q}/emf$ can vary with the mean temperature of the meter, the mean temperature being defined as $(T_2+T_1)/2$, where $T_2$ and $T_1$ are the temperatures at the respective major surfaces of the heat flow meter substrate panel. In order to account for this variation, the calibration procedure should include a series of measurements where $T_2-T_1$ is held constant while the mean temperature is varied and the voltage output measured. Furthermore, it may be necessary to account for possible variation in the calibration parameter with changes in heat flux. For this purpose, a further series of measurements can be conducted wherein the mean temperature is held constant while $T_2-T_1$ is varied and the voltage output measured. The results are then correlated and used to establish the relation between $\dot{q}/emf$ and the mean temperature.

A symmetric arrangement of thermocouples is provided on both major surfaces of the panel 18. These thermocouples are positioned at the points designated as 21 in FIG. 2. An identical arrangement of thermocouples is provided at the opposite surface of panel 18. The thermocouples monitor the surface temperatures of panel 18 in order to determine the uniformity of temperature across the heat flow metering area and to permit an accurate determination of heat flow through the meter based on the aforementioned calibration.

Referring again to FIGS. 1 and 3, the apparatus 10 is shown to also include a test simulation layer 22 affixed in face-to-face relation with layer 16. Layer 22 serves as a substrate for a cluster of heat flow sensors, each illustrated as a thin disk 23. As aforementioned, the test simulation layer is preferably constructed of the same material as the experimental substrate. Its exposed, lower surface, designated as 24 in FIG. 3, is the test simulation surface which is to simulate the surface of the experimental substrate. Accordingly, in its composition, emittance, geometry and other factors which influence heat transfer, this surface replicates the experimental substrate surface as closely as possible. As shown in the FIGURES, the apparatus is constructed such that heating element 12, conductive layer 15, heat flow meter 17, and sensors 23 are superposed to provide an effectively linear pathway for heat flow from element 12 to sensors 23.

The heat flow sensors 23 can be affixed to the simulation surface 24 by mechanical means, such as a support clip, but preferably are affixed by means of a small amount of grease or other jelly-like substance placed between the facing surfaces of the sensor and simulation layer. Where mechanical means are used, it is still preferred to use such a grease or jelly, in order that a secure and continuous junction is provided which promotes uniform heat flow to the sensor across its entire surface. A preferred material for this purpose is a silicone grease such as Dow High Vacuum Grease, Compound #9.

A plurality of sensors can be affixed to the simulation layer 24, as illustrated, provided that they are placed in that area of the layer surface which underlies the area of heat flow meter 17 i.e., underlies the heat flow metering area. The sensors can be calibrated simultaneously provided that sufficient data gathering capability is available.

For purposes of support and protection of the system, a rigid, protective upper layer 25 is superposed over and affixed to the upper surface of insulating layer 11. The layer 25 can be comprised of any suitably protective material such as a wood panel, gypsum board, polymer composite panel, and the like. Affixed to layer 25 are structural angles 26 which serve as a means for attachment of the assembled apparatus to the experimental substrate. Layer 25 can be affixed to structural angles 26 by an adhesive.

FIG. 3 provides a sectional, side elevational view of the calibration apparartus 10 with the respective components assembled and bonded into an integral laminate. Insulation layers 11 and 16 are in superposition and brought into proximate, face-to-face relation, i.e., their facing surfaces are separated only by the thin elements and any bonding materials placed therebetween, together with any entrained air. The bond 27 which is provided over the peripheral border area between the layers can be formed by any suitable bonding agent such as an epoxy adhesive. Prior to bonding these layers about their periphery, the heat conducive layer 15 is bonded to the facing surface of heat flow meter 17 using a thin layer of epoxy (not shown) and the heating element 12 is bonded to the opposite face of layer 15, also using a thin layer of epoxy (not shown). Protective layer 25 is similarly bonded to the facing surface of insulating layer 11. The assemblage is sealed and protected about its edges and across the upper, exposed surface of the layer 25 by applying an epoxy shell 28 thereto. Leads 14 from heating element 12 extend between layers 11 and 16 to the edge of the assembly, through the epoxy shell, and to a variable power source (not shown). Leads 20 and the leads from the thermocouples of the heat flow meter also extend between layers 11 and 16, through the epoxy shell, and to a datalogger (not shown).

The insulation layers used in the present apparatus should provide enough resistance to heat flow to establish a temperature differential across the thickness of the layer, and particularly across the thickness of the heat flow meter, which is sufficient to generate a measurable voltage output by the heat flow meter. Although the minimum measurable voltage will vary depending on the sensitivity of monitoring equipment, it generally is preferred to have a temperature differential capable of generating at least 0.1 mv. in the meter. The insulating layers should also, however, permit a degree of heat flow which approximates that expected for the experimental substrate on which heat flow measurements are to be made and which is sufficient to prevent any undue temperature increase in the apparatus which could damage either the heater element or the insulating layers. In general, insulating layers with an R value in the range of 1 to 6 are preferred. Insulating layers having R values within this range have been found to provide desired temperature differentials and heat flow while permitting the use of desirably thin layers of about 1 in inch in thickness. Thinner insulation layers are preferred since they minimize lateral heat loss and allow fabrication of an apparatus with a relatively thin profile. This latter feature allows placement of the apparatus, particularly the test simulation surface and the heat flow sensors mounted thereon, in close proximity to the experimental substrate.

The insulation layers should be thermally stable under the conditions of use and stable under normal conditions of storage in order to insure that their heat transfer properties remain unchanged. This insures that the heat flow meter calibration parameter remains unchanged. Preferably, the layers are formed from a rigid insulating polymeric foam or plastic panel, and most preferably, an expanded polystyrene foam panel. Polystyrene panels having densities in the range of 1.2 to 1.7 have been found to be particularly advantageous.

In order to promote heat flow in the direction of the heat flow meter, the R value of layer 11 should be at least as great as that of layer 16. In general, it is preferred that layers 11 and 16 be comprised of the same material and have the same thickness and, thus, provide the same R value.

A preferred heating element for use in the apparatus is that which comprises a flexible layer of lamellar graphite with copper conductive strips affixed adjacent to opposing sides of the graphite sheet, e.g., as shown in FIG. 1. This assembly is then bonded between two layers of dielectric polyester. Heating elements of this type are manufactured by TVI Energy Corporation, Bettsville, Md. 20705, and have a thickness of about 0.005 in.

The heating element should be capable of providing uniform heat flows over a range approximating that which is anticipated in the experimental substrate. In general, heating elements capable of providing uniform heat fluxes through the heat flow metering area of about 2 to about 15 BTU/h.ft$^2$ are satisfactorily employed for calibration purposes.

As previously noted, the heating element is preferably slightly larger than the heat conductive layer and heat flow metering area. In the preferred construction, the heat flow metering area measures one foot by one foot (primarily for purposes of permitting calibration of the heat flow meter in the Dynatech Rapid k) and the conductive layer is also one foot square. The heating element measures about 13 inches square such that it extends beyond and folds downward over the edges of the conductive layer, contacting the lower insulation layer as shown, for example, in FIG. 3.

The heat conductive layer can be made of any material which satisfactorily distributes heat evenly over the heat flow metering area. A thin heat conductive metal plate, e.g., with a thickness of 0.02 to 0.1 in., is preferred, and most preferably a copper or aluminum plate.

The test simulation substrate can be affixed to the facing surface of the insulation layer and inserted heat flow meter by any suitable means. It is generally preferred to bond the substrate to the insulation layer with a thin layer of an adhesive such as an epoxy or to mechanically fasten the substrate to the insulation layer with a grease such as a silicone grease spread over the total area of the substrate. This method of affixing the substrate provides a uniform, continuous air free junction which can facilitate a steady and uniform heat flow to the substrate.

The use of adhesives, greases, etc. for bonding the test simulation substrate to the lower insulation layer is preferred where the substrate comprises a pre-formed material such as steel or aluminum sheeting or gypsum board. However, where it is possible to mold or cast the substrate onto the insulation layer without damage to that layer, and, in this manner, upon setting of the substrate material, bond the substrate material to the layer, it is generally preferred to employ the casting or molding operation as a means of incorporating the substrate into the apparatus. In general, the bond formed between the substrate and the insulation layer will be a continuous and air free bond with preferred heat transfer capabilities. Use of the molding or casting operation can also prove to be a simpler and more reliable means of attachment, particularly where the substrate is not readily bonded using conventional adhesives. The casting or molding method is especially advantageous in the case of hydraulic cementitious materials. Hydraulic cements or concretes may be cast directly onto the polystyrene foam panel preferred for use in this invention in order to form substrates which simulate cement or concrete roofdecks and the like. The cement or concrete forms an intimate bond with the polystyrene and thus provides a uniform heat transfer boundary between the respective layers.

The heat flow sensors are mounted in that area of the test simulation surface which is in alignment with or beneath the heat flow metering area. This area is herein referred to as the "test metering area" of the test simulation surface. Normally, three to eight sensors are mounted within a one square foot test metering area on the test simulation surface and simultaneously calibrated, i.e., the voltage outputs of the sensors are measured simultaneously and thereafter used to determine a calibration parameter for the sensors.

Although any of the commercially available heat flow sensors can be used in the invention, heat flow sensors manufactured by Technisch Physische Dienst, P. O. Box 155, Delft 2208, Netherlands, as Model No. WS 21 HT were found to meet sensitivity, precision, and size requirements and were used for experimental purposes.

As previously noted, the heat flow sensors are preferably mounted on the test simulation surface by means of a thin layer of grease or other jelly-like substance to provide a secure and continuous, air free connective junction. Leads from the heat flow sensors should be taped or otherwise connected to the substrate surface a short distance from the sensor in order to maintain a sound bond between the sensor and substrate surface.

Figure 4:
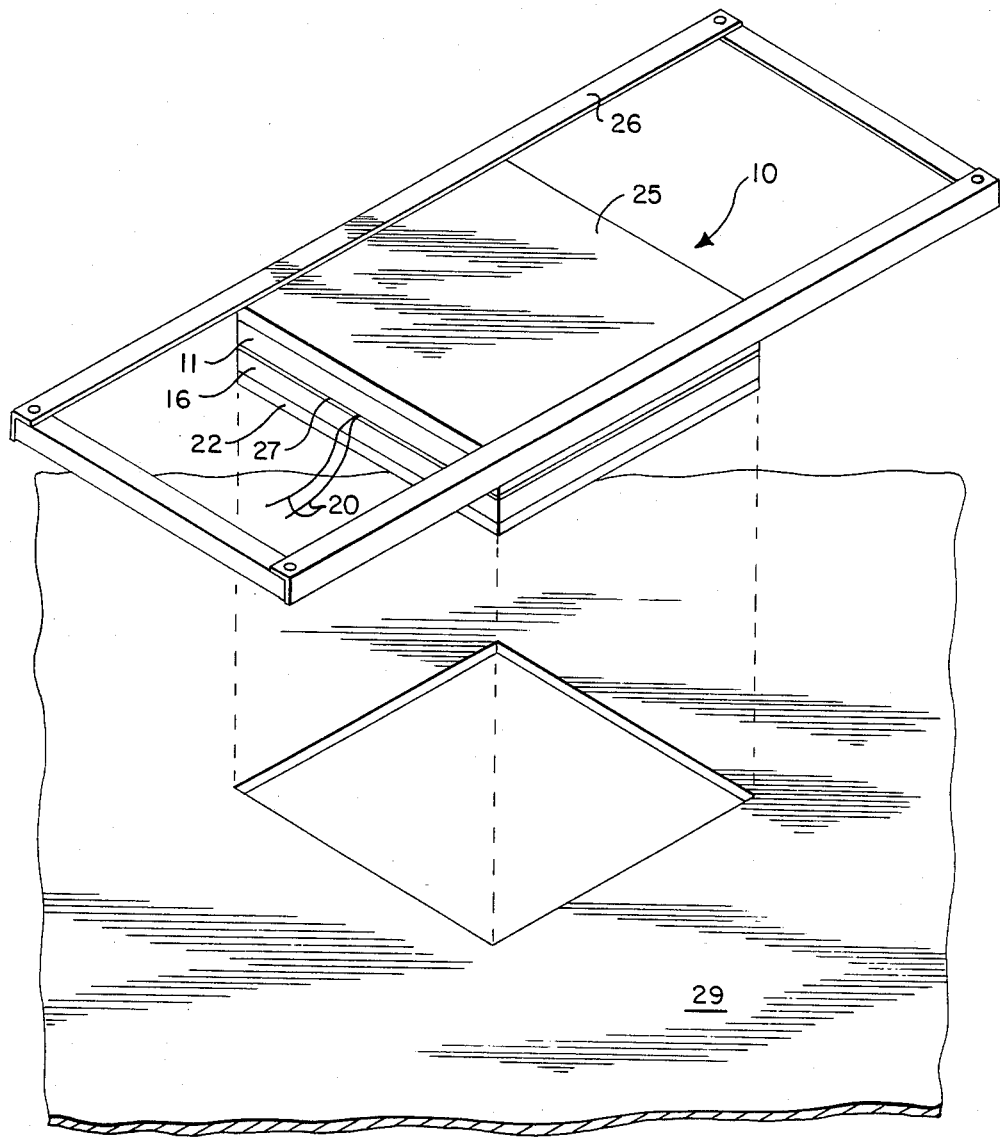
FIG. 4 is an exploded, perspective view of an additional preferred embodiment of the apparatus of this invention.

FIG. 4 illustrates a preferred system in which the calibration apparatus 10 is fitted with an apron 29 to effectively extend the test simulation surface 22 over a larger area, thereby providing a closer replication of the experimental surface, in terms of its actual area. The use of the apron allows fabrication of a relatively compact apparatus, preferably measuring about two feet on a side, while allowing calibration under conditions which more closely replicate the heat transfer environment to be encountered by the sensor in experimental measurements. The lower surface of the apron is placed coplanar with the test simulation surface and has the same geometry, e.g., in the case of a corrugated steel deck, it has the same corrugation pattern so as to provide a continuation of each of the corrugations in the test simulation surface. While the apron can be fabricated from the same materials as surface 22, it is preferably fabricated from a lightweight foam such as an expanded polystyrene foam panel, in order to provide a lightweight construction which can be satisfactorily retained about the apparatus by simple friction fitting. The foam is either painted the same color as the test simulation surface or, in the case of a cementitious test simulation surface, coated with a thin layer of the cementitious material.

The apron preferably increases the effective simulation surface area to about 16 square feet (4 ft.×4 ft.). For example, in the preferred construction where the heat flow metering area and test metering area are each one foot square, the test simulation surface area of the apparatus measures about 4 square feet (2 ft.×2 ft.) and the apron increases this area to about 16 square feet.

As illustrated in FIG. 4, the apron is cut out at its center so as to be friction fitted about the test simulation substrate.

The apparatus of this invention is mounted in the closest possible proximity to the intended experimental measurement area for purposes of calibration of the heat flow sensors. Wherever possible, it is mounted directly over or suspended directly beneath the experimental measurement area. Once mounted, calibration is initiated by providing various uniform heat flows through the heat flow meter using a variable power source for the heating element. Generally, the temperatures generated in the vicinity of the heating element and conductive plate will range from about 80° F. to 135° F. with an apparatus constructed of the preferred high density polystyrene insulation layers and provide heat flux through a one foot by one foot heat flow metering area of about 2 to 15 BTU/h ft². For each level of heat flow, sufficient time should be allowed to reach a "steady state" where heat flowing through the test simulation substrate is the same as that flowing through the heat flow meter.

The steady state heat flows are measured by means of the voltage output of the heat flow meter. Simultaneously, the surface temperatures of the heat flow meter are measured by means of the voltage output of the thermocouples affixed thereto and the voltage outputs of the heat flow sensors are also monitored and recorded. This data can be collected and recorded using a multi-channel datalogger such as the Fluke Model 2200B Data Logger manufactured by John Fluke Manufacturing Co. Inc. The voltage output of the heat flow meter is converted to a quantitative heat flux on the basis of the calibration parameter for the meter, taking into consideration the variation of this parameter as a function of the mean temperature of the meter, thus providing $\dot{q}$. The voltage output (emf) of the heat flow sensors in response to this $\dot{q}$ provides the desired calibration parameter, $\dot{q}$/emf, for the heat flow sensor. This calibration parameter, i.e., the response of the heat flow sensor to a certain $\dot{q}$, can vary as a function of the convective and radiative heat transfer environment in which the sensor is placed, and also as a function of the mean temperature of the sensor, this latter variation being analogous to that discussed above in relation to the heat flow meter. Accordingly, and in accordance with the method aspects of this invention, the air and surface temperatures in the vicinity of the sensors are also measured simultaneously with the measurements of the voltage outputs of the calibration apparatus. These air and surface temperatures should include those of the test simulation surface and also air temperatures within 3 inches of the heat flow sensor cluster. It is also preferred to monitor air and surface temperatures further removed from the apparatus. For example, where the apparatus is suspended from the ceiling of a room, the temperatures of the walls and floor of the room should be measured as well as representative air temperatures throughout the volume of the room. These air and surface temperature measurements characterize the convective and radiative heat transfer environment of the heat flow sensors during calibration and provide an additional set of variables which are considered in the calibration of the heat flow sensors. $\dot{q}$/emf is thus determined for a given set of heat transfer environmental conditions. Preferably, a sufficient number of measurements are taken over an adequate period of time to either determine that these environmental conditions are essentially invariant or to determine the q̇/emf for the variant conditions which can occur in the vicinity of the experimental substrate. These determinations are necessary in order to properly evaluate heat flow sensor output under experimental conditions and ensure that the appropriate calibration parameter is applied to the sensor voltage output to establish q̇. The replication of the experimental substrate by the test simulation substrate is important to this aspect of the experimental measurement process in that it reproduces the convective and radiative conditions which can influence q̇/emf.

After calibration of the heat flow sensor, the apparatus is removed, the sensors are removed from the test simulation surface, and the sensors are then mounted on the experimental substrate by the same means used for mounting on the test simulation surface. The voltage output of the sensors in response to heat flow through the experimental substrate is then measured, along with environmental air and surface temperatures (as during the calibration), and heat flow through the experimental substrate determined on the basis of the individual calibration parameter for each sensor.

The method of this invention is accordingly directed toward the measurement of heat flow through an experimental substrate surface employing a surface mounted heat flow sensor or cluster of heat flow sensors which have been calibrated to establish the relationship between heat flow through the surface and the resultant induced voltage output of the sensor under the convective and radiative heat transfer environmental conditions of the experimental substrate surface, measuring the voltage output of the sensor induced by heat flow through the substrate surface, and converting the voltage output to a quantitative heat flow on the basis of the calibration of the sensor. In a preferred practice, the method comprises the steps of mounting a heat flow sensor or, preferably, a cluster of heat flow sensors on a test simulation surface having a substantially identical geometric structure and substantially identical heat transfer characteristics as the experimental substrate; positioning the test simulation surface in proximity to the experimental substrate such that the test simulation surface and the heat flow sensors mounted thereon are exposed to the same heat transfer environment as that of the experimental substrate; providing different levels of uniform heat flow through the test simulation surface and measuring each level; measuring the individual voltage output of the heat flow sensors in response to each of the different heat flow levels and simultaneously measuring air and surface temperatures in the environment of the heat flow sensors; determining a calibration parameter, which defines the relationship between heat flow through the test simulation surface and the resultant voltage output of the heat flow sensors, as a function of the measured air and surface temperatures; removing the heat flow sensors from the test simulation surface; mounting the sensors on the experimental substrate by the same means used to mount the sensors on the test simulation surface; measuring the voltage output of the heat flow sensor in response to heat flow through the experimental substrate and simultaneously measuring air and surface temperatures on the environment of the heat flow sensor; and converting the measured voltage to a quantitative heat flow on the basis of the calibration parameter.

In the preferred practice of using a cluster of sensors, a calibration parameter for the sensors is derived and used to convert the experimental voltage output of the sensors to a quantitative heat flow. In the event that the surface is flat, the average voltage output of the sensors is used in determining q̇/emf. Where the surface is corrugated, the projected surface area weighted average of the voltage output of the sensors is used.

As noted above in describing the apparatus of this invention, the test simulation surface should duplicate the experimental substrate surface as closely as possible in terms of emittance, composition, and geometry. The test simulation surface is the exposed surface of a test simulation substrate and, as aforementioned, the composition of this substrate is preferably a uniform and mechanically and thermally stable material.

It will be recognized that, in large measure, the present method involves the on site calibration of the heat flow sensors. The foregoing description of the apparatus of this invention, particularly in terms of its operation, should thus be understood as applicable to conducting the present method. Thus, variation of the heat flow between about 2 to about 15 BTU/h.ft$^2$ is generally satisfactory for the calibration steps of the present method and the surface temperature of the test simulation substrate and air temperatures within about 3 inches of the sensors should be measured, as well as representative surface and air temperatures throughout the enclosure of the experimental substrate.

Various aspects of the heat flow measurement method and calibration apparatus of this invention are described in the paper presented by R. D. Orlandi, L. S. Shu, G. D. Derderian, and B. Siadat at the American Society of Heating, Refrigerating, and Air-Conditioning Engineers/ Department of Energy Conference on "Thermal Performance of the Exterior Envelopes of Building II" on Dec. 8, 1982 in Las Vegas, Nev. under the title "A Field Thermal Measurement Technique For Building Envelope Systems". This paper was subsequently published in ASHRAE SP38, Proceedings of the ASHRAE/DOE Conference", in the summer of 1983. The entire disclosure of this paper is hereby expressly incorporated by reference into this application.

Materials suitable for use in the present invention and parameters such as calibration heat flow levels, heating element temperatures, voltage outputs, and the number of thermopile junctions and thermocouples used in the present apparatus can vary depending on the intended application and on such factors as datalogging capability and the sensitivity of appurtenant instrumentation. Accordingly, specific materials, quantities, and numeric ranges provided in the foregoing description are intended as illustrative and not limitative.

What is claimed is:

1. An apparatus for calibrating a heat flow sensor, said apparatus comprising:
    a first insulation layer;
    a second insulation layer having first and second major surfaces, said first major surface being in proximate, face-to-face relation with said first insulation layer;
    a heat flow meter located at an interior heat flow metering area of said second insulation layer;
    a heating element positioned between said first and second insulating layers and superposed with said heat flow metering area;
    a heat conductive layer having the same or larger dimensions than said heat flow metering area and superposed therewith, said layer being positioned between said heating element and said metering area;

means for monitoring the voltage output of said heat flow meter to permit measurement of heat flow across said heat flow metering area;

a test simulation substrate layer in proximate, face-to-face relation with said second surface of said second insulation layer and comprising an exposed test simulation surface comprising a test metering area having approximately the same dimensions as said heat flow metering area and superposed therewith; and a heat flow sensor affixed to said exposed test simulation surface within said test metering area.

2. An apparatus of claim 1 wherein said first and second insulation layers are each comprised of a polymeric foam panel.

3. An apparatus of claim 1 wherein said first insulation layer has an R value at least as great as that of said second insulation layer.

4. An apparatus of claim 1 wherein said heat flow meter comprises a substrate panel with a thermopile wrapped thereabout, said substrate panel comprising the same material and having the same thickness as said second insulation layer and being closely fitted into a central aperture in said second insulating layer.

5. An apparatus of claim 4 comprising a copper-constantan thermopile wrapped about said substrate panel so as to provide the same symmetric distribution of copper-constantin junctions at both major surfaces of said panel.

6. An apparatus of claim 5 further comprising a plurality of thermocouples symmetrically and identically positioned on both major surfaces of said panel.

7. An apparatus of claim 1 wherein said heat conductive layer is comprised of a heat conductive metal plate.

8. An apparatus of claim 7 wherein said metal plate is a copper or aluminum plate.

9. An apparatus of claim 1 wherein said heat conductive layer is bonded to said heat flow meter, said heating element is bonded to said heat conductive layer, and said first and second insulation layers are bonded to each other about a peripheral area of their facing surfaces.

10. An apparatus of claim 1 wherein said heating element comprises a thin sheet of lamellar graphite and two copper conductive strips bonded to the graphite adjacent opposing edges of the graphite sheet.

11. An apparatus of claim 1 further comprising a rigid support layer affixed to said first insulation layer opposite said second insulation layer.

12. An apparatus of claim 1 further comprising an apron having the same geometric construction as said test simulation surface and closely fitted about said apparatus to provide a continuation of said test simulation surface.

13. A method of measuring heat flow through a surface of an experimental substrate comprising the steps of:

mounting a heat flow sensor on a test simulation surface having a substantially identical geometric structure and substantially identical heat transfer characteristics as said surface of said experimental substrate;

positioning said test simulation surface in proximity to said experimental substrate such that said simulation surface and said heat flow sensor are exposed to the same heat transfer environment as that of said surface of said experimental substrate;

providing different levels of uniform heat flow through said test simulation surface and measuring each level of heat flow;

measuring the voltage output of said heat flow sensor in response to each of the different heat flow levels and simultaneously measuring air and surface temperatures in the environment of said heat flow sensor;

determining a calibration parameter from the measured heat flow and voltage output, which defines the relationship between heat flow through said test simulation surface and the voltage produced thereby in said heat flow sensor, as a function of the measured air and surface temperatures;

removing said heat flow sensor from said test simulation surface;

mounting said heat flow sensor on said surface of said experimental substrate by the same means used to mount said sensor on said test simulation surface;

measuring the voltage output of said heat flow sensor in response to heat flow through said surface of said experimental substrate and simultaneously measuring air and surface temperatures in the environment of said heat flow sensor; and converting the measured voltage produced in said heat flow sensor to a quantitative heat flow on the basis of said calibration parameter.

14. A method of claim 13 wherein said heat flow through said test simulation surface is varied within the range of about 2 to about 15 BTU/h.ft$^2$.

15. A method of claim 13 wherein the surface of said experimental substrate and said test simulation surface are of the same emittance and comprise the same materials.

16. A method of claim 13 wherein a plurality of heat flow sensors is mounted on said test simulation surface and said calibration parameter is determined for each sensor.

17. A method of claim 13 wherein said means for mounting said sensor comprises a grease or jelly-like substance which provides a uniform, continuous junction between said sensor and said test simulation surface.

18. A method of claim 13 wherein the respective simultaneous measurements of air and surface temperatures in the environment of said heat flow sensor include measurements of the surface temperatures of said experimental substrate and said test simulation surface and measurements of air temperatures within about 3 inches of said sensor.

19. A method of measuring heat flow through the surface of a substrate comprising the steps of calibrating a heat flow sensor to establish the relationship between heat flow through said surface and the resultant induced voltage output of said sensor under the variant radiative and convective heat transfer environmental conditions of said surface, mounting said sensor on said surface, measuring the voltage output induced in said sensor by heat flow through said surface, and converting said voltage output to a quantitative heat flow on the basis of the calibration of said sensor.

* * * * *